United States Patent [19]

Tokumi et al.

[11] Patent Number: 4,758,084
[45] Date of Patent: Jul. 19, 1988

[54] APPARATUS FOR DETECTING DEFECTS ON A BOTTLE MOUTH WITH A SCREW THREAD

[75] Inventors: Akira Tokumi; Hiroyuki Fukuchi; Kazushi Ishikawa, all of Tokyo, Japan

[73] Assignee: Kirin Beer Kabushiki Kaisha, Tokyo, Japan

[21] Appl. No.: 883,544

[22] Filed: Jul. 8, 1986

[30] Foreign Application Priority Data

Jul. 10, 1985 [JP] Japan ................... 60-150021

[51] Int. Cl.⁴ ............................................. G01N 21/90
[52] U.S. Cl. ................................ 356/237; 250/223 B; 356/240; 358/106
[58] Field of Search ............... 356/237, 239, 240, 390; 250/223 B; 209/526; 358/106

[56] References Cited

U.S. PATENT DOCUMENTS

| | | | |
|---|---|---|---|
| 4,284,353 | 8/1981 | Yoshida et al. | 250/223 B X |
| 4,391,373 | 7/1983 | Wiggins | 356/240 X |
| 4,435,641 | 3/1984 | Hajime | 250/223 B |
| 4,606,635 | 8/1986 | Miyazawa et al. | 250/223 B X |

FOREIGN PATENT DOCUMENTS

60-98340  6/1985  Japan ................... 356/240

Primary Examiner—Vincent P. McGraw
Attorney, Agent, or Firm—Ladas & Parry

[57] ABSTRACT

An apparatus for detecting defects on a bottle mouth has an annular illuminator, a reflecting mirror for forming a planar image of the bottle mouth, a CCD camera for detecting the planar image and an operation unit for operating electric signals produced by the CCD camera to judge existence of the defects on the bottle mouth. Detecting operation of defects can be carried out instantly without rotating the bottle.

5 Claims, 9 Drawing Sheets

APPARATUS FOR DETECTING DEFECTS ON A BOTTLE MOUTH WITH A SCREW THREAD

BACKGROUND OF THE INVENTION

This invention relates to an apparatus for detecting defects on a bottle mouth with a screw thread and particularly to an apparatus capable of detecting defects on the entire periphery of a bottle mouth without rotating the bottle by forming concentric planar optical images of the bottle mouth.

Some of glass bottles for liquor or soft drink, newly manufactured or recovered from market for reuse, have flaws, scratches or cracks on their bottle mouths. These defects cause incompletely airtight sealing of a bottle mouth and sanitary problems with respect to liquor or soft drink thereafter sealed in the bottles. Accordingly, it is necessary to detect such defects on the mouths of these bottles to omit those bottles with defects.

Various methods of detecting defects on a bottle mouth have been proposed. In each method, however, the bottle is rotated through 360° to detect the whole screw thread about the bottle mouth, and the image of the entire screw thread is formed through a linear senser or TV camera. The image of the screw thread is converted into electric signals to be processed.

In these conventional methods, therefore, a mechanism for rotating each bottle to be detected is indispensable and causes a complex structure, increases the number of structural members and raises the manufacturing cost. Further, as the entire part of a screw thread is detected during one rotation of each bottle, the entire part thereof cannot be detected instantly. Therefore, a great number of bottles cannot be detected in a short time.

SUMMARY OF THE INVENTION

It is an object of this invention to provide an apparatus for detecting defects on a bottle mouth with a screw thread, which can detect instantly even a small defect anywhere on the entire periphery of the bottle mouth without rotating the bottle and which has a simple construction.

According to this invention, there is provided an apparatus for detecting a defect on a bottle mouth having a screw thread around an inner or outer surface thereof. It has an annular illuminator disposed over a bottle to be detected for illuminating the entire periphery of the mouth of the bottle. Optical means form a planar image of the bottle mouth in by changing light rays emitted in different, i.e. various, directions from the inner and outer surfaces of the bottle mouth are changed into light rays parallel with each other. Two-dimensional photoelectric converting means converts a planar image of the bottle mouth from the parallel light rays into corresponding electric signals corresponding to each divided portion of the planar image and a judging unit processes the electric signals to detect the existence of any defect on the bottle mouth or, more specifically the screw thread thereof.

BRIEF DESCRIPTION OF THE DRAWINGS

The foregoing objects and other objects as well as characteristic features of the invention will become more apparent from the following detailed description and the appended claims when read in conjunction with the accompanying drawings, wherein:

DETAILED DESCRIPTION OF THE INVENTION

Figure 1:
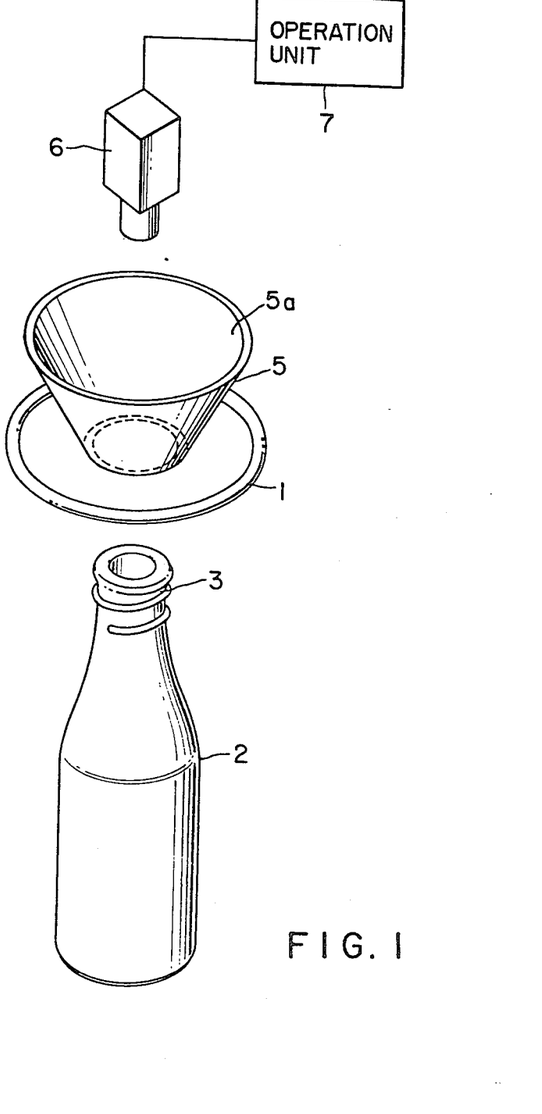
FIG. 1 is a perspective view showing a schematic construction of this invention.

FIG. 1 shows a basic structure of an apparatus for detecting defects on a mouth with a screw thread of a bottle. An annular illuminator 1 is disposed over a bottle 2 so that the axis of the round mouth 3 of the bottle 2 coincides with the axis of the annular illuminator 1. The annular illuminator 1 may be formed in such a manner that a plurality of light sources each emitting a beam of light (light beam) are disposed annularly or may be an annular light source emitting uniformly diffused light. The relative positional relationship between the annular illuminator 1 and the bottle 2 to be detected and directions in which light beams are cast on the surface of the bottle 2 are properly selected depending on what method is adopted for detecting defects on the mouth 3 of the bottle 2. Over the annular illuminator 1 is disposed a reflecting mirror 5 having an inner reflecting surface 5a in the form of an inverted truncated cone in such a manner that the axis of the mirror 5 is coincided with the axis of the annular illuminator 1. The images of respective portions of the mouth 3 are formed concentrically on the mirror 5.

Further, over the reflecting mirror 5 is disposed a CCD camera 6 (charge-coupled device camera) as a two-dimensional photoelectric converter in which, for instance, a plurality of photoelectric converting elements are arranged in a matrix pattern of 100 rows × 100 columns. The photoelectric converting elements produce picture element signals corresponding to the brightness levels of respective portions of an image formed thereon by the mirror 5.

The CCD camera 6 is connected to an operation unit 7 which processes picture element signals produced by the CCD camera 6 thereby to judge existence of defects on the bottle mouth 3.

A principle of forming two concentric circular images of the bottle mouth 3 will now be explained.

Figure 2:
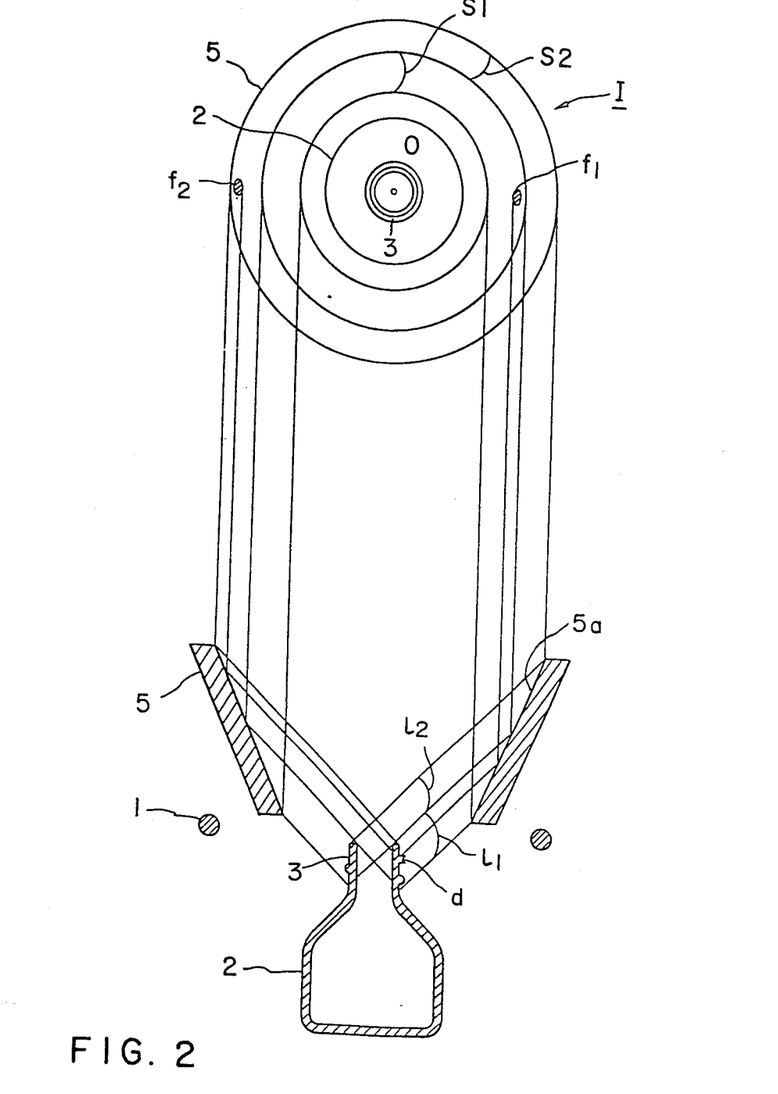
FIG. 2 is schematic elevation, partly in section showing the way in which a planar image (burned 90°) of a bottle mouth is formed.

FIG. 2 is a view for showing an image of the bottle mouth formed on the reflecting mirror 5 disposed over the bottle 2 and having an inner reflecting surface in the form of an inverted truncated cone. In FIG. 2, a light bundle or rays $l_1$ on a certain vertical plane emitted from the outer surface of the bottle mouth 3 goes obliquely upwardly and reflects on the reflecting surface 5a of the mirror 5 thereby to change its course into the vertical direction. As the axes of the bottle mouth 3 and the mirror 5 coincide with each other, all light bundles emitted from the entire outer peripheral surface of the bottle mouth 3 having a screw thread d reflect on the mirror 5 to go vertically upwardly in the same manner as the light bundle $l_1$. Accordingly, a circular image $S_1$ of the outer surface of the bottle mouth 3 is formed as viewed from the bottom in FIG. 2, but turned in FIG. 2 90° to be shown, in which, of course the image (not shown) of the screw thread is a spiral. The image $S_1$ is located in the inner region in FIG. 2, but turned in FIG. 2 90° to be shown, in which, of course, the image (not shown) of the screw thread is a spiral. In contrast, a light bundle $l_2$ emitted from the inner surface of the bottle mouth 3 also goes obliquely upwardly and reflects on the mirror 5 thereby to change its course into the upper direction. Thus, a circular image $S_2$ of the inner surface of the bottle mouth 3 is formed as viewed in the lower direction. The image $S_2$ is located in the outer region adjacent to the inner region where the image $S_1$ is formed in FIG. 2 and the above two images $S_1$, $S_2$ are concentric with each other. In this manner, the image of the bottle mouth 3 has a shape such that the inner and outer surfaces of the bottle mouth 3 are unfolded concentrically. If, for example, there is a defect d on the outer surface of the bottle mouth 3, an image $f_1$ is viewed in the inner region $S_1$ and an image $f_2$ is viewed in the outer region $S_2$. In this manner a defect forms two images $f_1$, $f_2$ in their respective regions $S_1$, $S_2$ and the two images $f_1$, $f_2$ are located on the same diameter line (line passing by the center O of the image I). That is, in FIG. 2, the defect image $f_1$ is formed by light emitted from the outer surface of the bottle mouth 3 while the defect image $f_2$ is formed by light passing through the wall of the bottle mouth 3.

FIGS. 3 through 8 are views for showing an embodiment in which the images of defects to be detected are brightened in the dark image $I_1$ (FIG. 5) of the inner and outer surfaces of the bottle mouth 3 when a plurality of light beams emitted from an annular illuminator 30 are cast on the bottle mouth 3 in its tangential direction.

Figure 3:
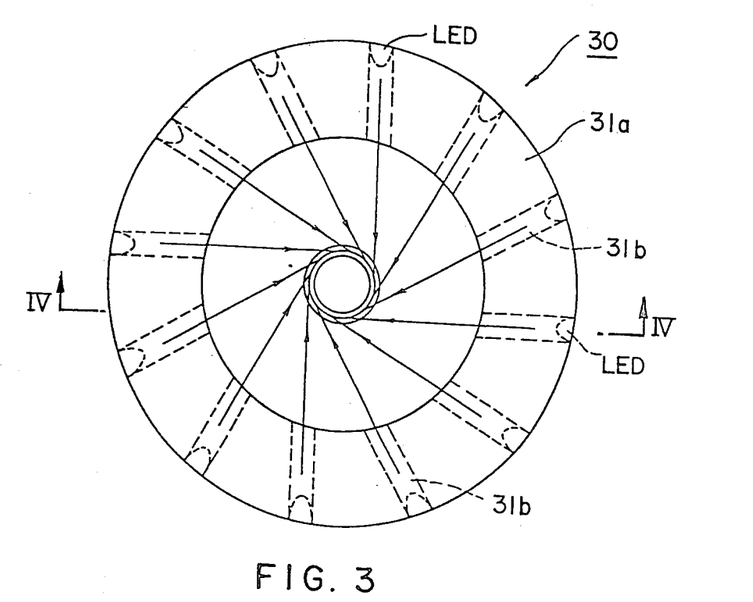
FIG. 3 is a plan view of an annular illuminator used in the invention.

FIG. 3 is a plan view of an annular illuminator 30 having a plurality of slits 1b, 1b, . . . 1b which are disposed at a certain space interval in an annular body 31a. The slits 31b are directed obliquely downward in the tangential direction of the bottle mouth 3, respectively, and the outer end of each slit 31b has a light emitting diode (LED) therein.

Figure 4:
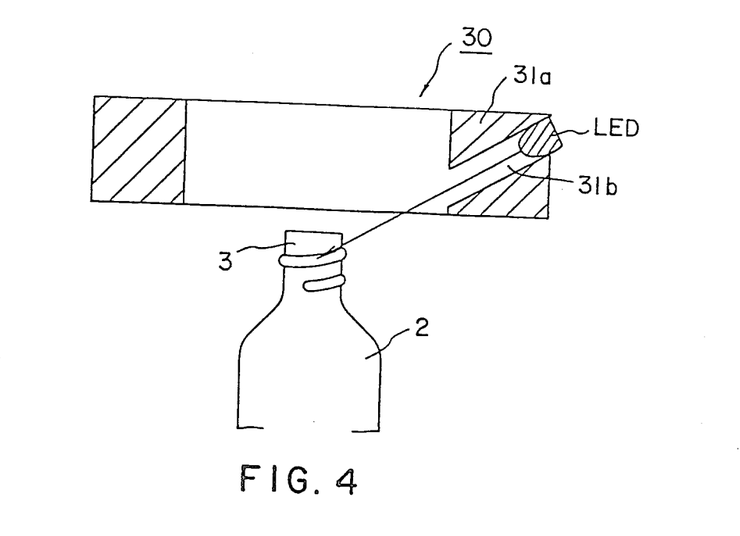
FIG. 4 is a vertical sectional view taken along the line IV—IV in FIG. 3.

The illuminator 30 for producing a plurality of light beams is not limited to the structure shown in FIGS. 3 and 4. That is, any type of illuminator in which diffused lights emitted from a light source are focused by some lenses may be used. Lights having a directivity such as laser light can be substituted for the light beams. In addition, lights emitted from a light source may be focused by a reflecting mirror to form light beams.

Figure 5:
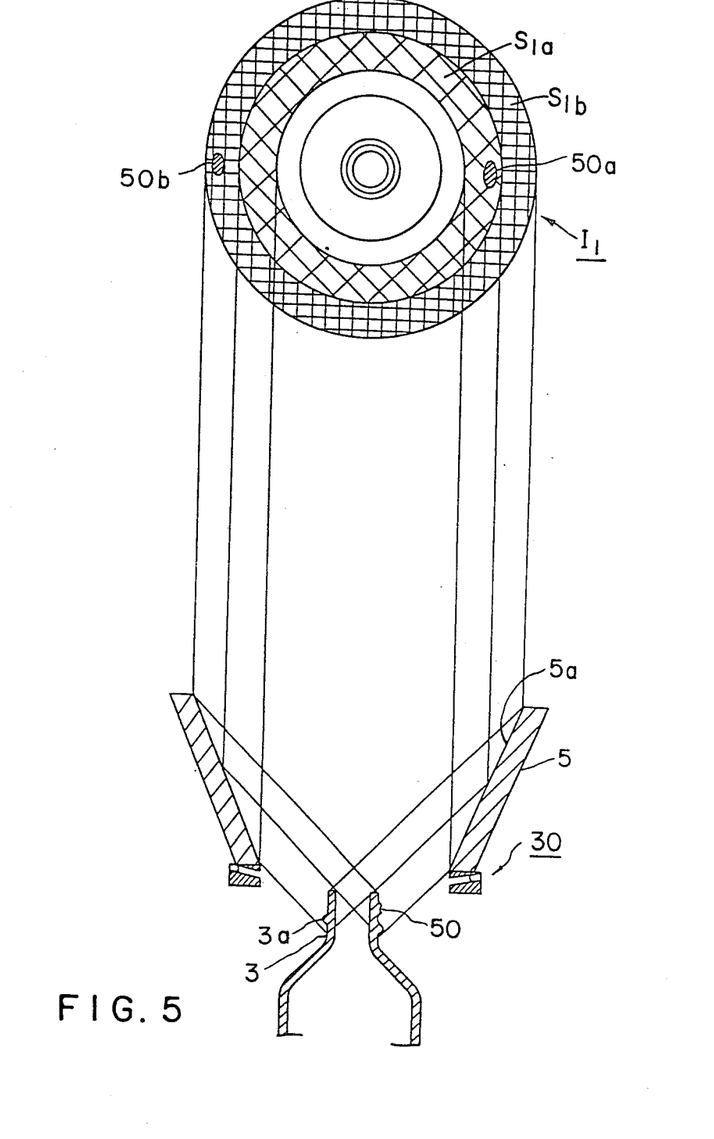
FIG. 5 is a view showing a state wherein another planar image of a bottle mouth is formed.

In this case, if the surface of the bottle mouth 3 is smooth, that is, the surface thereof has no defects, the light beams are reflected on its surface in accordance with their angles of incidence, respectively, and accordingly each reflected light beam does not reach the reflecting mirror 5. However, if there is a defect 50 on the bottle mouth 3, light beams are irregularly reflected on an irregular surface of the defect 50 and part of the diffused light beams reaches the reflecting surface 5a to form two bright defect images 50a, 50b in the surface images $I_1$. In general, the bottle mouth 3 does not necessarily have a completely uniform surface and accordingly, in actuality, light beams are slightly irregularly reflected on the bottle mouth 3. The reflected light beams reach slightly the mirror surface 5a to form two dark images $S_{1a}$, $S_{1b}$ as shown in FIG. 5. Accordingly, the outer circular image $S_{1b}$ corresponding to the inner surface of the bottle mouth 3 is formed outside the inner circular image $S_{1a}$ corresponding to the outer surface of the bottle mouth 3 in a concentric manner therewith.

Accordingly, the two images 50a, 50b of the defect 50 on the bottle mouth 3 shine brightly on the background of the less bright (dark) circular images $S_{1a}$, $S_{1b}$. The CCD camera 6 detects the defect images 50a, 50b and the two concentric images $S_{1a}$, $S_{1b}$ to produce a lot of picture element signals corresponding to brightness level of those images through a lot of photoelectric converting elements disposed in a matrix pattern.

The picture element signals are operated by the operation unit 7 to judge whether or not the bottle mouth 3 has defects.

Figure 6:
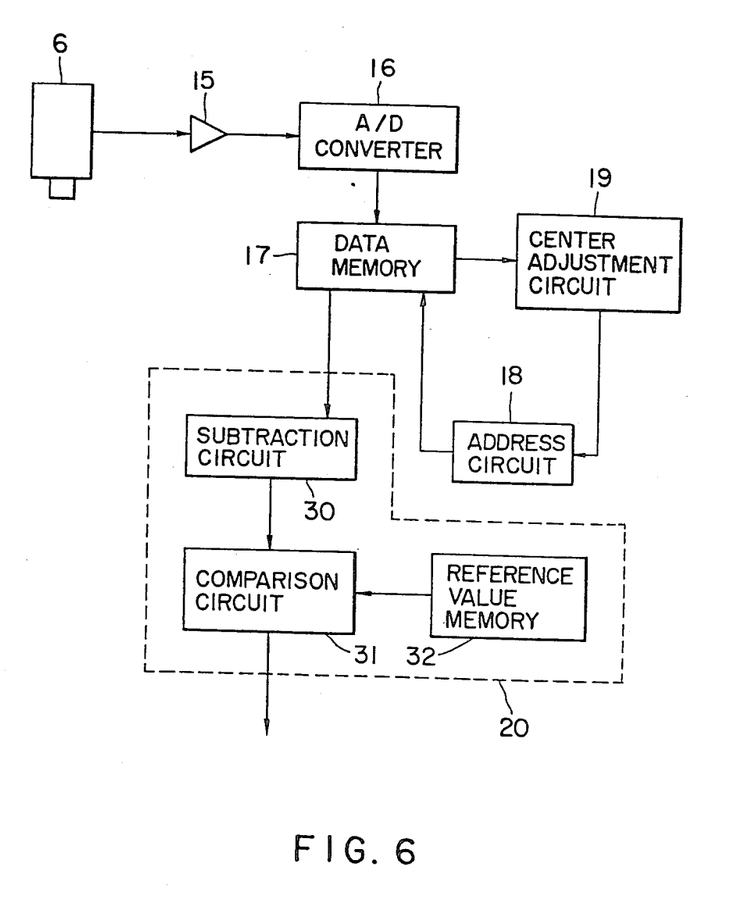
FIG. 6 is a block diagram of an operation unit connected to a CCD camera.

The operation unit 7 will next be explained with reference to FIG. 6.

The images obtained by the CCD camera 6 are scanned continuously to output picture element signals (electric signals corresponding to brightness levels of the image of the picture element signals) which are then amplified by an amplifier 15. The signals amplified thereby are converted from analogue signals into digital signals through an analog-to-digital converter 16 and then are memorized as data electric signals in portion corresponding addresses of a data memory 17, respectively. Address signals are input into the data memory 17 through an address circuit 18 in order to read out data therein and data read out of the memory 17 are output to a judging circuit 20.

The picture elements of the photoelectric converter are disposed in a matrix pattern of 100 rows × 100 columns for instance. Signals for showing brightness level of each picture element are quantized into 64 values to produce digital signals of 6 bits. When the value is 0, the image is darkest while when the value is 64, the image is brightest. A value of each picture element is memorized in an address of the memory 17 corresponding to a position of the picture element.

Judgement of existence of defects will next be explained.

Figure 7:
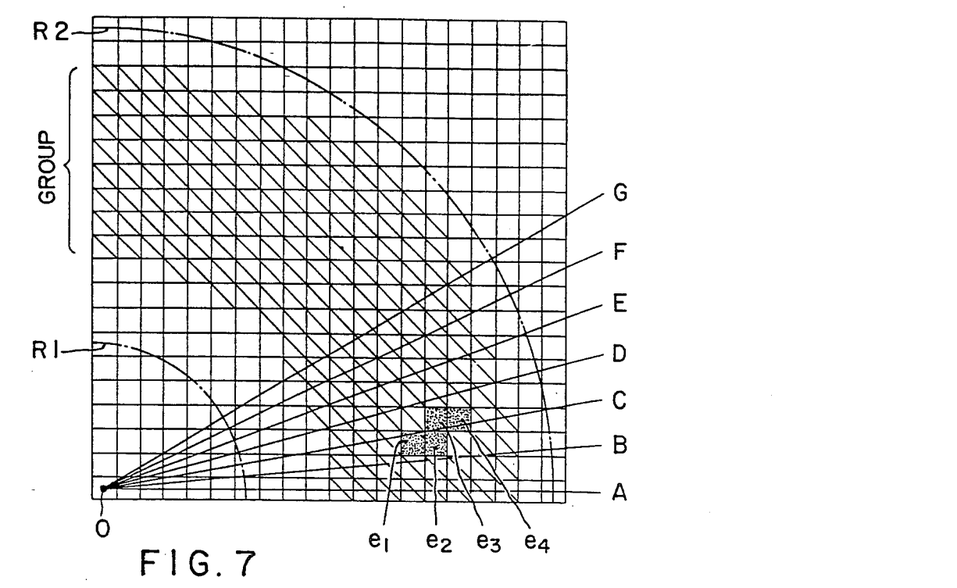
FIG. 7 is a view showing a method of reading out data memorized in a data memory.

FIG. 7 shows a partial image of one fourth of an entire image formed by the CCD camera 6. Four picture elements $l_1$ to $l_4$ (dotted region) corresponding to a defect are bright, while a group (hatched region) including a great many picture elements except the four elements $l_1$ to $l_4$ is slightly bright or dark. The group corresponds to part of the image of the bottle mouth 3. These picture element signals are memorized in the form of digital signals in respective addresses of the memory 17 through the amplifier 15 and the analog-to-digital converter 16.

If the center of data memorized is deviated from a predetermined position O, the center of the memorized data is adjusted by a well known center adjusting circuit 19. The picture element signals are read out in response to address signals output from the address circuit 18. That is, a great many address (scanning) lines (OA, OB, ... OX) are determined, each extending from the center O in the radial direction and at an angular interval of 0.5° to each adjacent address line. The reading operation is carried out along each address line in the radial direction within a region between inner and outer arched lines $R_1$, $R_2$. The horizontal address line A is determined as a datum line and 720 address lines are determined at an angular interval of 0.5°. As a result, 720 groups of picture element signals corresponding to the same number of the address lines are produced. Then, the judging circuit 20 compares a signal of a picture element disposed at a certain distance from the center O on an address line with a signal of one of other picture elements disposed at the same distance as that of the former picture element from the center O on one of other address lines. That is, a subtraction between a signal of an "n"th picture element as counted from the inside of an address line and a signal of an "n"th picture element as counted from the inside of one of other address lines is carried out by a subtraction circuit 30. Such a subtraction is carried out with respect to all groups of picture element signals. Each difference between two signals is expressed by binary digits through a comparison circuit 31. That is, if the difference is larger than a reference value inputted from a reference value memory 32, the binary digital number is "1" while if the difference is smaller than the reference value, the binary digital number is "0".

Figure 8A:
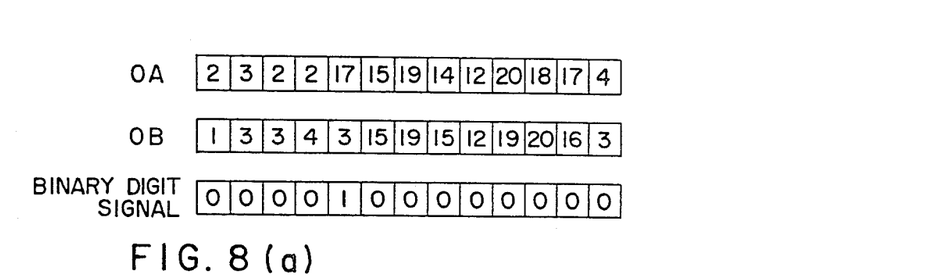
FIGS. 8(a) and 8(b) are diagrams showing a method of processing picture element signals, respectively.
Figure 8B:
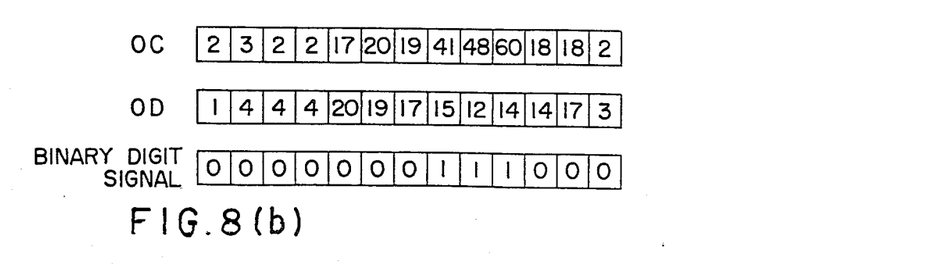

For example, the differences between the picture element signals on the address line OA and the picture element signals on the adjacent address line OB are shown in FIG. 8(a), respectively, while the differences between the picture element signals on the address line OC and the picture element signals on the address line OD are shown in FIG. 8(b).

Further, a counter 33 counts the number of "1", obtained by the comparing operation, indicating a large difference between two picture element signals on two different address lines. This counting operation is carried out with respect to all pairs of two adjoining address lines such as the address lines OA, OB; OB, OC; OC, OD; . . . . If the number of "1" is greater than a reference number, the judging circuit 20 outputs a number "1" which means existence of defects on the bottle mouth 3.

As the brightnesses of picture element signals at the same distance from the center O on different address lines are almost the same, the picture elements on two address lines properly selected may be compared with each other.

The above detecting method is suitable for the use of light beams as shown in FIGS. 3 and 4. In the case of using the light beams cast in the tangential direction of the bottle mouth 3, even if a defect such a flaw or scratch is very small or fine, the light beams are irregularly reflected on the defect and reach partially the mirror surface 5a to form a defect image. Accordingly, even such a small defect can be detected.

A modified embodiment of this invention will now be explained with reference to FIGS. 9 to 13. As there is apt to be a defect on a screw thread of the bottle mouth 3, detection of a defect on the screw thread should be mainly considered. In this modified embodiment, the annular illuminator 1 emitting diffused light is used as a light source to shine generally on the bottle mouth 3 and the image of a defect on a screw thread 4 of the bottle mouth 3 is formed darkly in a bright image of the screw thread 4.

Figure 9:
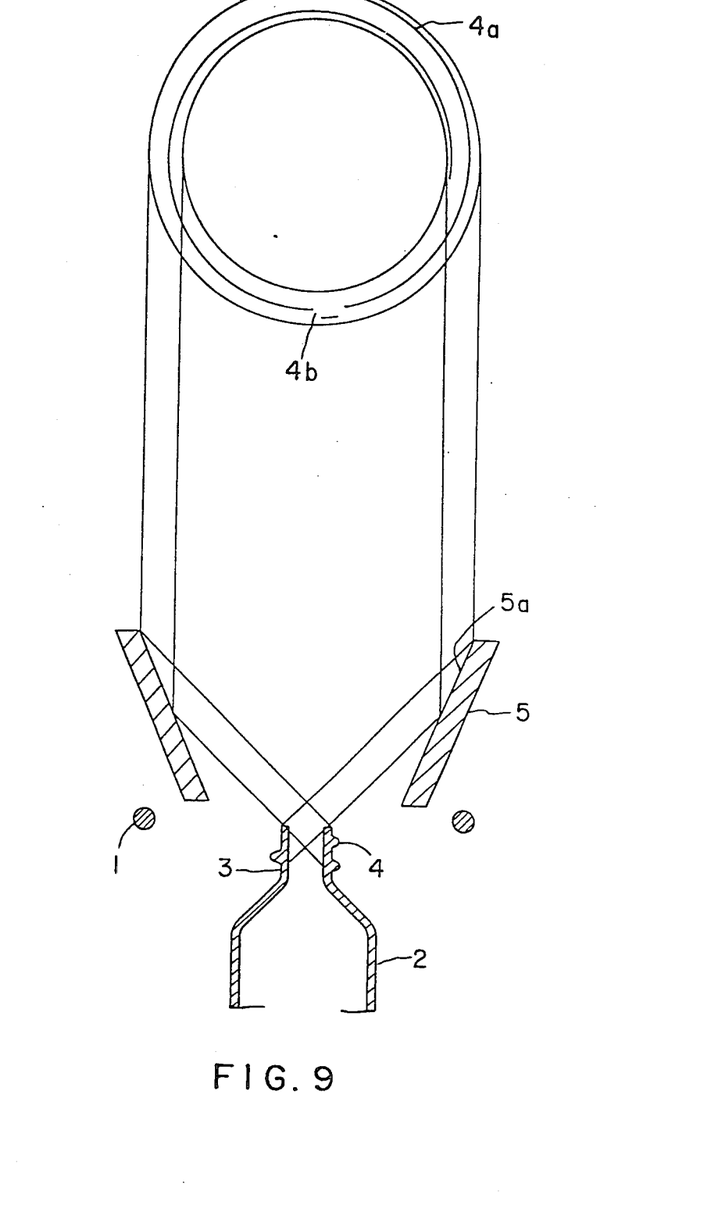
FIG. 9 is a view showing a state wherein the image of a screw thread on the bottle mouth is formed.

In FIG. 9, the diffused light emitted from the annular illuminator 1 is reflected on the screw thread 4 to form an image on the mirror 5. When the mirror surface 5a is viewd in the lower direction from upside, the image of the screw thread 4 can be seen brightly in the form of a spiral. If there is a defect on the screw thread 4, the diffused light is irregularly reflected on the defect to reach scarecely the mirror surface 5a.

Accordingly, the image 4a of the screw thread 4 has a cut portion 4b therein. The image 4a having the cut portion 4b is detected by the CCD camera 6 to produce each picture element signal corresponding to brightness of each portion of the screw thread 4 through photoelectric converting elements disposed therein in a matrix pattern. The picture element signals are processed by the operating unit 7 to judge existence of defects.

Figure 10:
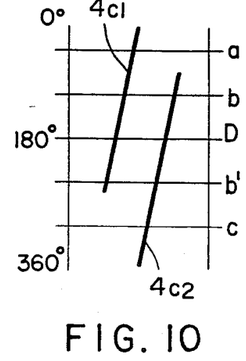
FIGS. 10 to 12 are views showing a state wherein the image of the screw thread is unfolded in a rectangular coordinates, respectively.
Figure 11:
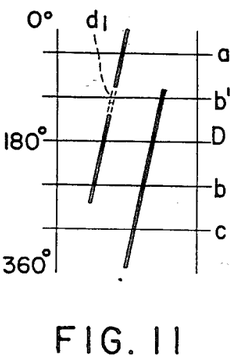
Figure 12:
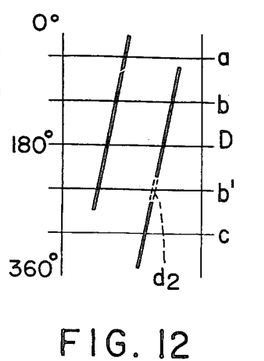

That is, analog signals of the picture elements are converted into digital signals through the analog-to-digital converter 16 to be memorized at their corresponding addresses of the data memory 17. Further, the address circuit 18 outputs each address signal to the data memory 17 and the judging circuit 40 reads out digital data in the data memory 17 from the center of their disposed pattern in the radial direction as shown in FIG. 7. Each of digital data read out is compared with a reference value inputted from a reference value memory 41 (FIG. 13) through a comparison circuit 42 to produce binary digital signals. This binary digital signals are converted by a coordinates transforming circuit 43 into digital binary signals in rectangular coordinates as shown in FIGS. 10 to 13 in each of which the ordinate axis indicates angular position and the abscissa axis indicates distance from a datum plane. That is, the image of the screw thread 4a is shown in a state wherein two divided inclined screw lines $4C_1$, $4C_2$ are disposed in their respective angular positions deviated slightly from each other. The digital binary signals converted by the coordinates transforming circuit 43 are converted into analog images through a D/A converter 45 as shown in FIGS. 10 to 12.

Figure 13:
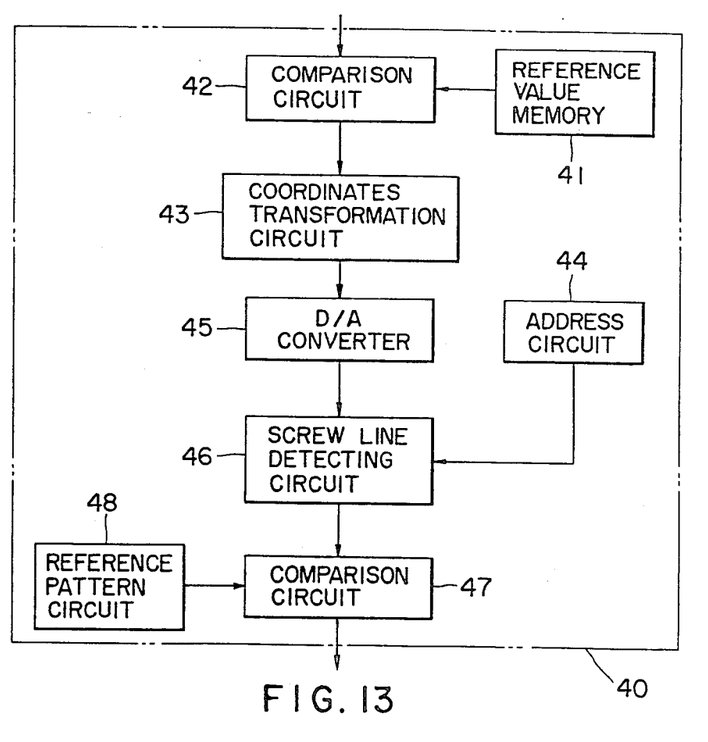
FIG. 13 is a block diagram of another embodiment of a judging circuit of the judging unit.

A screw line detecting circuit 46 detects the two image lines $4C_1$, $4C_2$ in the horizontal direction at a predetermined angular interval in response to address (scanning) signals from an address circuit 44.

FIG. 10 shows the image of a normal screw thread 4a. In this case, a detecting means of the judging circuit 40 detects one screw image line $4C_1$ along a detecting line a and one screw image line $4C_2$ along a detecting line c while the detecting means detects two screw image lines $4C_1$, $4C_2$ along three detecting lines b, D, b'. That is, in the case of a normal bottle, the output pattern of the number of screw image lines to be detected is in the form of "1,2,2,2,1". If there is a defect on the bottle mouth 3, the image of the defect is expressed in the form of a cut portion $d_1$ or $d_2$ as shown in FIG. 11 or 12, respectively. In the case of FIG. 11, output pattern is in the form of "1,1,2,2,1". In the case of FIG. 12, the pattern is in the form of "1,2,2,1,1". Then, each output pattern is compared with the normal output pattern inputted from a reference pattern circuit 48 to detect existence of defects on the screw thread 4 through a comparison circuit 47.

Figure 14:
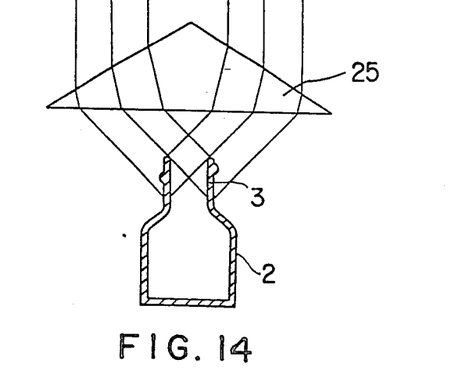
FIGS. 14 and 15 are schematic views showing other embodiments of optical means for forming a planar image of the bottle mouth, respectively.

In the above embodiments, a reflected mirror with a mirror surface in the form of an inverted truncated cone is used as an optical means for forming a planar optical image of a bottle mouth. However, the optical means is not limited to those of the embodiments. For example, a prism 25 having an isosceles triangle in section can be used. The prism 25 can refract lights from the bottle mouth 3 so that the lights go upward in parallel with each other. As a result, concentric images of the bottle mouth 3 are formed.

Figure 15:
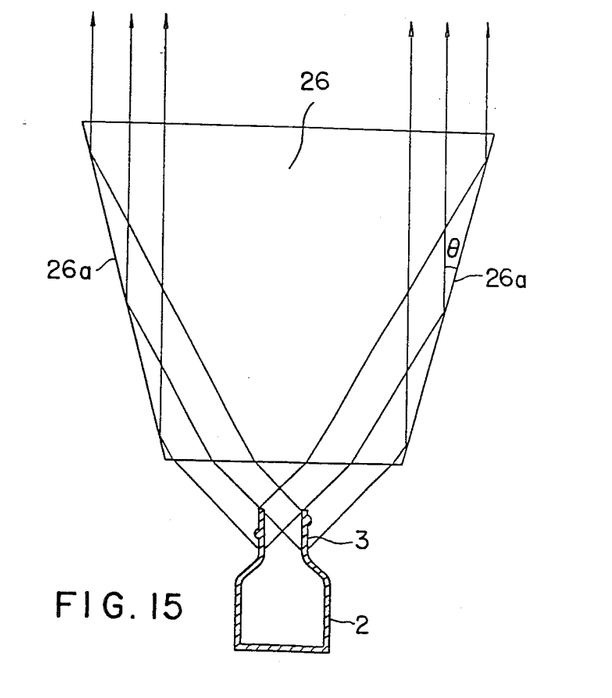

Further, a prism 26 with an inverted trapezoid section may be also used. In this prism 26, lights from the bottle mouth 3 are completely reflected on the inclined side surfaces 26a, 26a so that the lights go upward in parallel with each other. Also in this case, concentric images of the bottle mouth 3 are formed. Instead of the above operation unit 7, other operation means can be also used.

In the above manner, in this invention, as the images of the inner and outer surfaces of a bottle mouth are formed concentrically by a reflected mirror or prism, the whole portion of the bottle mouth can be detected instantly without rotating each bottle. Accordingly, a mechanism for rotating each bottle is not necessary thereby to cause a simple construction of the apparatus for detecting defects. Further, as the concentrical images of the bottle mouth are converted by a converter into electric signals, a great many bottles can be detected for a short time.

What is claimed is:

1. An apparatus for mainly detecting defects on a screw thread disposed around a bottle mouth, which comprises:
   (a) an annular illuminator disposed over a bottle to be detected for emitting diffused light to shine the entire periphery of the mouth of a bottle;
   (b) optical means for forming a spiral image of the screw thread in such a manner that lights reflected on the screw thread are changed into lights parallel with each other;
   (c) a two-dimentional photoelectric converter for converting the spiral image into electric signals corresponding to respective portions of the signal image; and
   (d) a judging unit for operating the electric signals to judge existence of defects on the screws thread, the judging unit comprising: a data memory for memorizing data of brightness level inputted from the two-dimensional photoelectric converter in respective addresses corresponding to each portion of the bottle mouth; an address circuit for reading out data memorized in the data memory along a plurality of address lines disposed an angular interval and extending from the center of disposition of data in the radial direction; a comparison circuit for comparing each value read out of the data memory with a reference value to express each compared value as binary digit; a coordinates transformation circuit for converting binary digital signals obtained by the comparison circuit into analog images of the screw thread in a rectangular coordinates; a screw line detecting circuit detecting the analog images having a plurality of lines of the screw thread; and a comparison circuit for comparing a pattern detected by the screw line detecting circuit with a reference pattern.

2. An apparatus according to claim 1, wherein the screw line detecting circuit scans a plurality of lines of the screw thread in the rectangular coordinates in the horizontal direction.

3. An apparatus according to claim 1, wherein the optical means comprises a reflecting mirror having a reflecting inner peripheral surface in the form of an inverted truncated cone.

4. An apparatus according to claim 1, wherein the optical means comprises a prism for forming a planar image.

5. An apparatus for detecting a defect on a bottle mouth having a screw thread therearound, the apparatus comprising:
   an annular illuminator emitting diffused light for illuminating the entire periphery of a mouth of a bottle having a screw thread around at least one of inner and outer surfaces thereof, whereby light rays are emitted in various directions from the inner and outer surfaces of the mouth of the bottle;
   optical means changing suffient of the light rays emitted in the various directions from the inner and outer surfaces of the bottle into light rays parallel with each other for forming a planar image of at least the surface of the mouth of the bottle having the screw thread, whereby the planar image of the screw thread is a spiral;
   two-dimensional photoelectric converting means receiving at least the spiral planar image of the screw thread for converting the same into electric signals corresponding to brightness levels of respective portions thereof; and
   judging unit means processing the electric signals for detecting the existence of any defect on the screw thread, the judging unit means comprising:
   data memory means converting the electric signals into respectively corresponding data signals for memorizing the data signals at addresses respectively corresponding to the portions of the spiral planar image of the screw thread;
   address circuit means for reading each of the data signals memorized at the addresses in the data memory means along address lines, each address line extending from a center of the data signals memorized at the addresses in the data memory means and being at an angular interval to each of adjacent address lines;
   comparison circuit means for comparing a value of each read data signal with a reference value and expressing each compared value as a binary digit;
   coordinates transforming circuit means for converting the binary digits into analog image signals in rectangular coordinates, whereby the analog image signals represent inclined screw lines of the screw thread in respective angular positions;
   screw line detecting circuit means detecting the analog image signals along angularly-deviated image lines for obtaining a first pattern therefrom; and
   comparison circuit means for comparing the first pattern with a reference pattern, whereby defects may be detected.

* * * * *